US005771897A

United States Patent [19]
Zufrin

[11] Patent Number: 5,771,897
[45] Date of Patent: Jun. 30, 1998

[54] METHOD OF AND APPARATUS FOR QUANTITATIVE EVALUATION OF CURRENT CHANGES IN A FUNCTIONAL STATE OF HUMAN ORGANISM

[76] Inventor: Alexander Zufrin, 15 Davis Rd., Acton, Mass. 01720

[21] Appl. No.: 629,138

[22] Filed: Apr. 8, 1996

[51] Int. Cl.$^6$ ...................................... A61B 5/002
[52] U.S. Cl. .......................... 128/670; 128/630; 128/700; 128/716
[58] Field of Search .................... 128/630, 670, 128/671, 696, 700, 731, 716, 732, 733, 721; 364/413.02, 413.05, 413.06

[56] References Cited

U.S. PATENT DOCUMENTS

| | | | |
|---|---|---|---|
| 5,255,186 | 10/1993 | Steinhaus et al. | 128/700 |
| 5,282,474 | 2/1994 | Valdés et al. | 128/670 |
| 5,479,932 | 1/1996 | Higgins et al. | 128/671 |
| 5,511,553 | 4/1996 | Segalowitz | 128/696 |
| 5,574,641 | 11/1996 | Kawakami et al. | 128/700 |
| 5,584,297 | 12/1996 | Bodóet et al. | 128/700 |

*Primary Examiner*—Jennifer Bahr
*Assistant Examiner*—Bryan K. Yarnell
*Attorney, Agent, or Firm*—Ilya Zborovsky

[57] ABSTRACT

A quantitative evaluation of current changes in a functional state of a human organism is performed by evaluation of characteristics of interaction processes of at least two different physiological systems of the organism.

18 Claims, 6 Drawing Sheets

1 - evaluation of working ability by the invented method
2 - control evaluation by psychophysiological test
3 - threshold 1 - evaluation of working ability by the invented method
2 - control evaluation by psychophysiological test
3 - threshold

METHOD OF AND APPARATUS FOR QUANTITATIVE EVALUATION OF CURRENT CHANGES IN A FUNCTIONAL STATE OF HUMAN ORGANISM

BACKGROUND OF THE INVENTION

The present invention relates to method of and apparatus for quantitative evaluation of current changes in functional state of human organism. It can be used for example in physiology and medicine for evaluation of current working capability of a console operator (a man who operates any kind of technical equipment), for investigation of the reaction of a human organism to the influence of different outside factors (i.e. medicine, alcohol, narcotics, etc.), as well as in the diagnostics of some functional disorders in a human organism, etc.

Methods and apparatus for monitoring changes in a functional state of a human organism, which influence the professional activities of a person are generally known. These methods are based on simultaneous registration of various electrophysiological signals and physiological processes and on an independent analysis of these parameters. Such methods and apparatuses are disclosed for example in Ilyukhina V. A. Neurophysiology of the Functional States of a Human Being. Leningrad, Nauka, 1986; Rosekind M. R. et al. Fatigue in Operational Setting: Examples from the Aviation Environments. Human Factors, 1994, 36(2) :327–38; Trimol M. et al. Occurrence of Infraslow Potential Oscillations in Relation to Task Ability to Concentrate and Intelligence. In Int. J. Psychophysiology, 1990 9(2) :1667–70; and Wilson G. E., Fullenkamp P., David I. Evoked Potential, Cardiac, Blik and Respiration Measure of Pilot Work Load in Air-to-Ground Missions. Aviat. Space, and Environ. Med. 1994, 2:100–5.

However, the above mentioned methods and apparatuses only allow to obtain qualitative estimation of the functional state of a human organism. In some cases, they also make possible to reveal changes in the interconnection between the parameters of the analyzed signals that are related to solving of some intellectual problems, as disclosed for example Houts C. R., Raskin D. C., Kircher J. C. Mental and Physical Countermeasures Reduce the Accuracy of Polygraph Tests. J. Appl. Physiol., 1994, 79(2):252–9.

There are also methods and apparatuses that provide quantitative estimation of the functional state of the human brain, that are based on a cross-correlation and cross-spectral analysis of signals, which however exclusively similar signals, in particular EEG signals of different leads. These methods are widely used in diagnostics of various brain diseases, as disclosed for example in Bekhtereva N. P. Healthy and Sick Brain of a Human Being. Moscow, Nauka, 1980. However, the methods based only on the cross-spectral and cross-correlation analysis of the similar signals EEG signals do not allow to obtain quantitative evaluation of the changes in the functional state of a practically healthy person that are caused by his professional activities.

SUMMARY OF THE INVENTION

Accordingly, it is an object of the present invention to provide a method of and an apparatus for quantitative evaluation of current changes in functional states of a human organism, caused for example by professional activities of a person or by the influence of different outside factors, as well as to solve certain problems of diagnostics.

In keeping with these objects and with others which will become apparent hereinafter, one feature of the present invention resides, briefly stated, in a method which comprises the steps of evaluating characteristics of interaction processes of at least two different physiological systems of the organism by means of analyzing parameters of electrophysiological signals and/or physiological processes characterizing these systems.

It is another object of the present invention to provide an apparatus of the above mentioned general type, which comprises means for evaluating characteristics of interaction processes of at least two different physiological systems of the organism by means of analyzing parameters of electrophysiological signals and/or processes characterizing these systems.

With the method and apparatus in accordance with the present invention, it is possible to monitor the characteristics of interaction between different physiological systems, which can be used as indicator systems for the evaluation of changes in a human organism. Indicator systems are systems in which the changes in characteristics of interaction processes reflect the change in the functional state of the human organism as a whole, in the process of solution of a given problem. Estimation of the characteristics of the interaction processes of different physiological systems can be performed by means of cross-correlation and cross-spectral analysis of any pair of electrophysiological signals that are generated by the physiological systems analyzed (EEG, EKG, GSR, EMG, etc.) and/or of parameters characterizing the physiological processes in these systems (frequency of respiration, temperature, hormone concentration, etc.). For example, if the central nervous, cardiovascular and respiratory systems are taken as indicator systems for evaluation of the deterioration of working capacity of a person caused by fatigue, it is necessary to carry out a joint analysis of EEG-EKG, EEG-respiration, EKG-respiration signals, or in other words to estimate the current values of cross-correlation and cross-spectral functions of these pairs of signals. However, electrophysiological signals and physiological processes differ both in their frequency characteristic and in their shape. Therefore, it is incorrect to use directly cross-correlation and cross-spectral analysis of the processes.

In order to overcome this principal limitation it is also proposed in accordance with the present invention to simultaneously estimate some universal characteristics that are similar to analyzed signals and processes. Relative characteristics, namely rhythmical components of the parameter variations that are isolated from the analyzed signals (processes) by means of their demodulation are used as universal characteristics. The cross-correlation and cross-spectral analysis of the relative characteristics (rhythmical components) is accurate. Consequently, the cross-correlation and cross-spectral analysis of the pairs of data arrays that are formed on the basis of the rhythmical components of the analyzed pairs of signals, make it possible to quantitatively evaluate the characteristics of interaction between the analyzed physiological systems. The cross-correlation and cross-spectral analysis of the data should be performed many times with the given time shift during the whole time interval, in the frame of which the evaluation of the changes in the functional state of a human organism is carried out.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
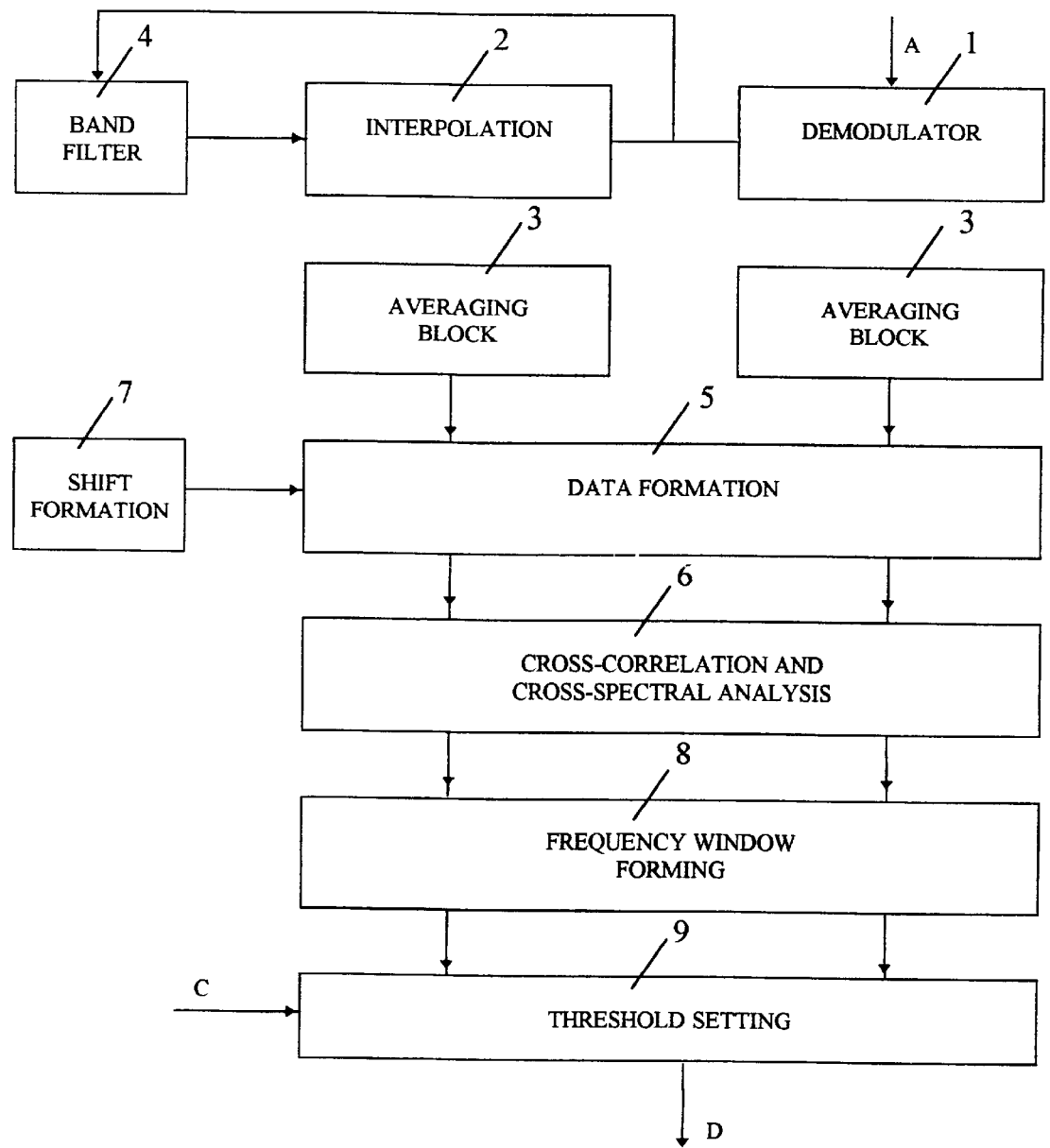
FIG. 1 is a flow chart illustrating a method of and an apparatus for quantitative evaluation of current changes in functional states of a human organism in accordance with the present invention.

The analyzed signals (processes) generated by the physiological systems, that are chosen to accomplish the given task, go to input A of the demodulator—block 1. The demodulator performs the isolation of the rhythmical components out of the variations of the parameters of the analysed signals by breaking up the signal into equidistant frames (e.g. Isec) and the preliminary calculating the average value for each frame. When analyzing the signals, it is taken into account that the parameters of some of them are incapable of having equidistant intervals by their nature (e.g. EKG, respiration, functioning the stomach). Demodulation of such signals is performed in their natural rhythm. However, later the isolated data are interpolated on the equidistant time intervals—block 2. When two signal are analyzed simultaneously, situations may occur in which the isolated rhythmical components will have equidistant, and not equal time intervals. To provide equality of their time intervals, the time averaging of each of these processes is done up to the corresponding time intervals—block 3.

It is known that the parameters of certain signals are modulated by other signals (e.g. EKG signals are modulated by respiration signals). Under the joint analysis of the two signals, one of which is modulated by the other one, it is possible not to use the channel of registration of the modulating signal, but to isolate it from the parameters of the modulated signal with the help of the corresponding analysis (e.g. to isolate the respiration signals from the EKG signals with the help of band filtration)—block 4. In the general case the isolated signal should undergo interpolation in block 3.

In order to perform the cross-correlation and cross-spectral analysis, it is necessary to form two data series with equal given duration (analysis epoch) and the same time start—block 5. The choice of the analysis epoch determines the lowest frequency of the frequency band, in the frames of which the spectral analysis is performed.

The cross-correlation and cross-spectral analysis is carried out in block 6. When choosing the formula of the cross-correlation and cross-spectral analysis, it should be kept in mind that modulation signals and interference do not belong to the class of stationary processes. Therefore the use of known formulas of correlation and spectral analysis does not provide the necessary validity and accuracy in spectral components estimation. Besides, the generally accepted formulas do not allow to maximally use the duration of the registered signals. To overcome these difficulties and to reduce the bias of estimates the following modified versions of the formulas are used:

calculation of the two-sided functions of the cross-correlation:

$$B_{xy}(\tau) = 1/N \sum_{K=0}^{N-1} X(k)Y(k+\tau), k+\tau \leq N;$$

$$B_{yx}(\tau) = 1/N \sum_{K=0}^{N-1} Y(k)X(k+\tau), k+\tau \leq N;$$

where:

X(K), Y(k)—the analyzed processes with duration T;

T=NΔt—the analysis epoch which determined the lowest frequency of the analyzed band (e.g. T=512 sec, or 1,024 sec);

N=2n—the number of discrete values, which determines the number of the partial filters under the spectral analysis (e.g. N=128, or 256);

Δt—the time interval between samples of an analyzed data array (e.g. Δt=4 sec, or 8 sec);

τ—discrete values of the temporary shift of the analyzed processes;

τ—0, 1, 2, . . . N)—1.

calculation of two-sided cross-spectra:
where:

$$A_{xy}(f_n)=F[B_{xy}(\tau)];$$

$$A_{yx}(f_n)=F[B_{yx}(\tau)];$$

F[ ]—operator of the fast Fourier transform (FFT);

n—numbers of the partial filters FFT; n=2 . . . N/2; for n={A(f_n)=0;

calculation of the resulting cross-spectra power:

$$P(f_n)=\sqrt{Axy(fn) \, Ayx(f_n)}.$$

To eliminate white noise, threshold limitation is introduced:

$$P(f_n) \geq \alpha Pmax(f_n);$$

where:

α—is the chosen threshold level (e.g. α=0.05, or 0.1).

To evaluate the current parameter changes of the interaction of the analyzed physiological systems, the procedure of the cross-correlation and cross-spectral analysis is carried out many times. Every time the beginning of the data arrays is shifted by a given time intervals compared to the previous one (e.g. 16 sec, or 32 sec). The repeated procedures above mentioned are conducted in the whole time interval, in which the current characteristics values of the systems interactions are determined (e.g. for 30 min., or 8 hours)—block 7.

Under real conditions, the change in the functional state of an organism, conditioned by the given task, is revealed only in one or several frequency windows. Therefore, in the analyzed frequency windows, the spectral components are summarized at the output of partial filters FFT (e.g. from filters n=2 to filters n=10, and from filters n=25 to filters n=40). When the spectral components are summarized, in order to increase the validity of the measured data, not all the spectral components, but only the most significant ones in the given frequency window, i.e. the components with the power exceeding the given level (e.g. level 0.25 or 0.4 of the maximal component), are taken into account—block 8.

When certain practical tasks are being accomplished, it is necessary to fix the time moment, at which the evaluated change in the functional state of the organism reaches a given level (e.g. the evaluated decrease of working capacity reaches the given average possible value). For this purpose, in block 9, the current values of the average power in each frequency window are compared with the threshold level (input B). The results of such a comparison determine the decision whether the achievement of the evaluated change in the functional state of the given value (output C) has been attained.

Examples of the inventive method and operation of the inventive apparatus are presented hereinbelow and illustrated on the subsequent figures.

The separation of the variations of parameters of various electrophysiological signals and physiological processes is performed by means of demodulation. It is necessary to take into consideration differences in the nature and time parameters of the processes and signals to be analyzed.

Figure 2:
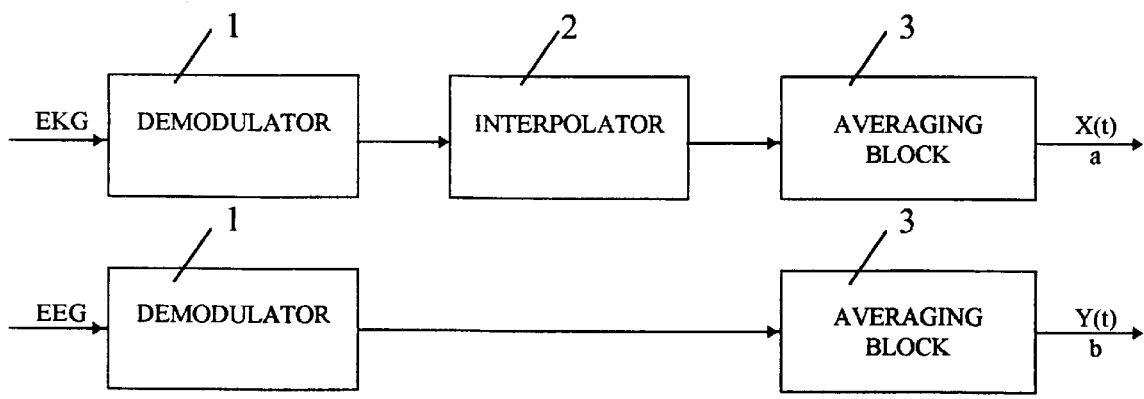
FIG. 2 is a view showing an example of a flow chart for separation of rhythmical components from electrophysiological signals generated by a central nervous system (EEG) and cardiovascular system (EKG)

The example in FIG. 2 is illustrated by the flow chart of the preliminary processing of the signals of EKG and EEG for their subsequent joint analysis. Under the demodulation of the EKG signals which are supplied from the output of the electrocardiograph, the simplest approach is to analyze variations of current values of R—R intervals. In this case the demodulation performed in the block 1 includes separation of R peak and measurements of R—R intervals. Taking into consideration the discrete nature of the EKG signals, in order to provide the subsequent cross-correlation and cross-spectral analysis, it is necessary to perform the interpolation of the measured values in selected equidistant time intervals, for example 1 second, in the block 2.

For a joint analysis of the EKG and EEG signals, it is necessary to provide the equal intervals of their averaging after the demodulation. In view of this, after the interpolation of the R—R intervals, it is necessary to provide an additional averaging in a time interval equal to the averaging time of signals EEG, for example 4 seconds or 8 seconds.

Under the demodulation of the EEG signals supplied from the output of the electroencephalograph and having uninterrupted nature, the variations of the average level of signal power over a selected time are analyzed, for example 4 seconds. The procedure of the demodulation of the signal EEG includes the operation of square detecting in block 1. The subsequent averaging is performed within 4 seconds in the block 3.

Figure 3:
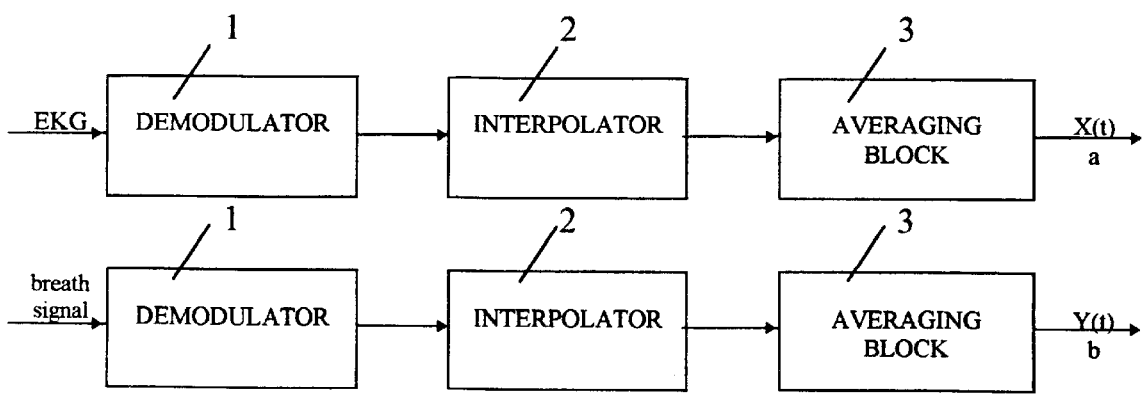
FIG. 3 is a view showing a flow chart of separation of rhythmical components from the signal EKG and the respiration signal with use of two independent sensors.

FIG. 3 shows the procedure of the preliminary processing, which precedes the joint analysis of the EKG signals and the respiratory process, with the use of the respiratory sensor. In this case all operations of processing of the EKG signals are identical to those described above, see FIG. 2. The process of respiration is converted by the respiration sensor into an uninterrupted electrical signal. The demodulation of this signal includes the measurement of variations of respiration periods in block 1. The obtained discrete data of the current values of respiratory periods must be interpolated in the selected equidistant intervals, for example 2 seconds, since the respiratory process is slower than the heart rhythm. In order to provide the equal time intervals of the analyzed signals, it is advantageous to maintain the averaging over the time of 4 seconds in block 3.

Figure 4:
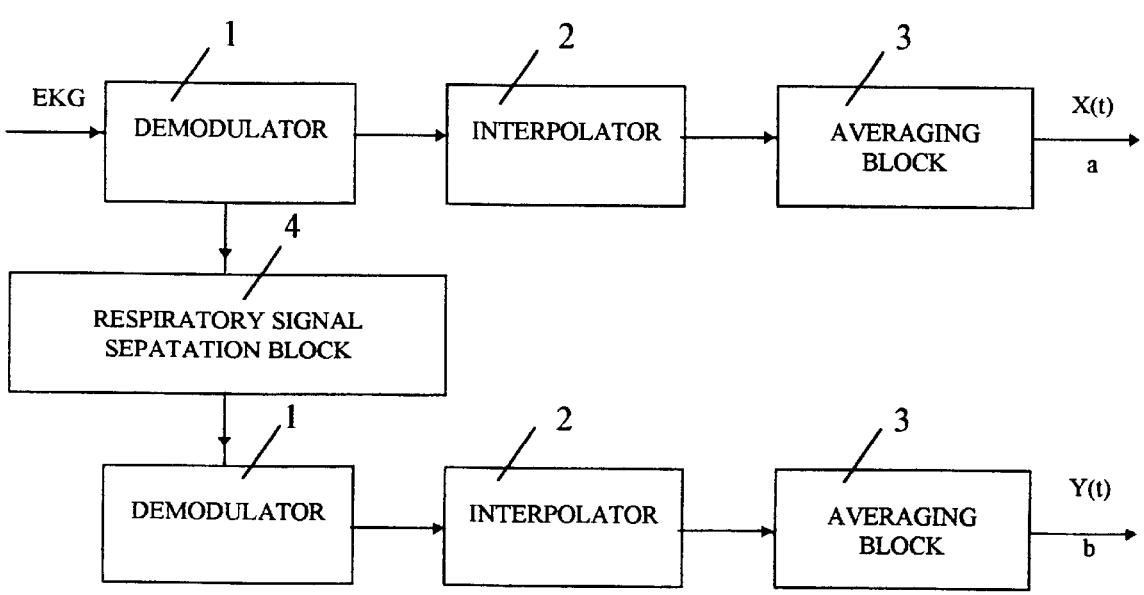
FIG. 4 is a view showing a flow chart of separation of rhythmical components from a signal EKG and a signal of respiration with use of only one sensor of EKG signal, in which the signal of respiration is separated from the EKG signal by filtering.

FIG. 4 shows an example of the flow chart of the preliminary processing under the joint analysis of the EKG signals and respiration without the use of a special respiratory sensor. In this case the respiration signals are separated from the variations R—R of intervals of the EKG signals by means of band filtration in block 4. The block 1 is a demodulator, the block 2 is an interpolator, the block 3 is a device for averaging analogous to the corresponding blocks of FIG. 3.

Figure 5:
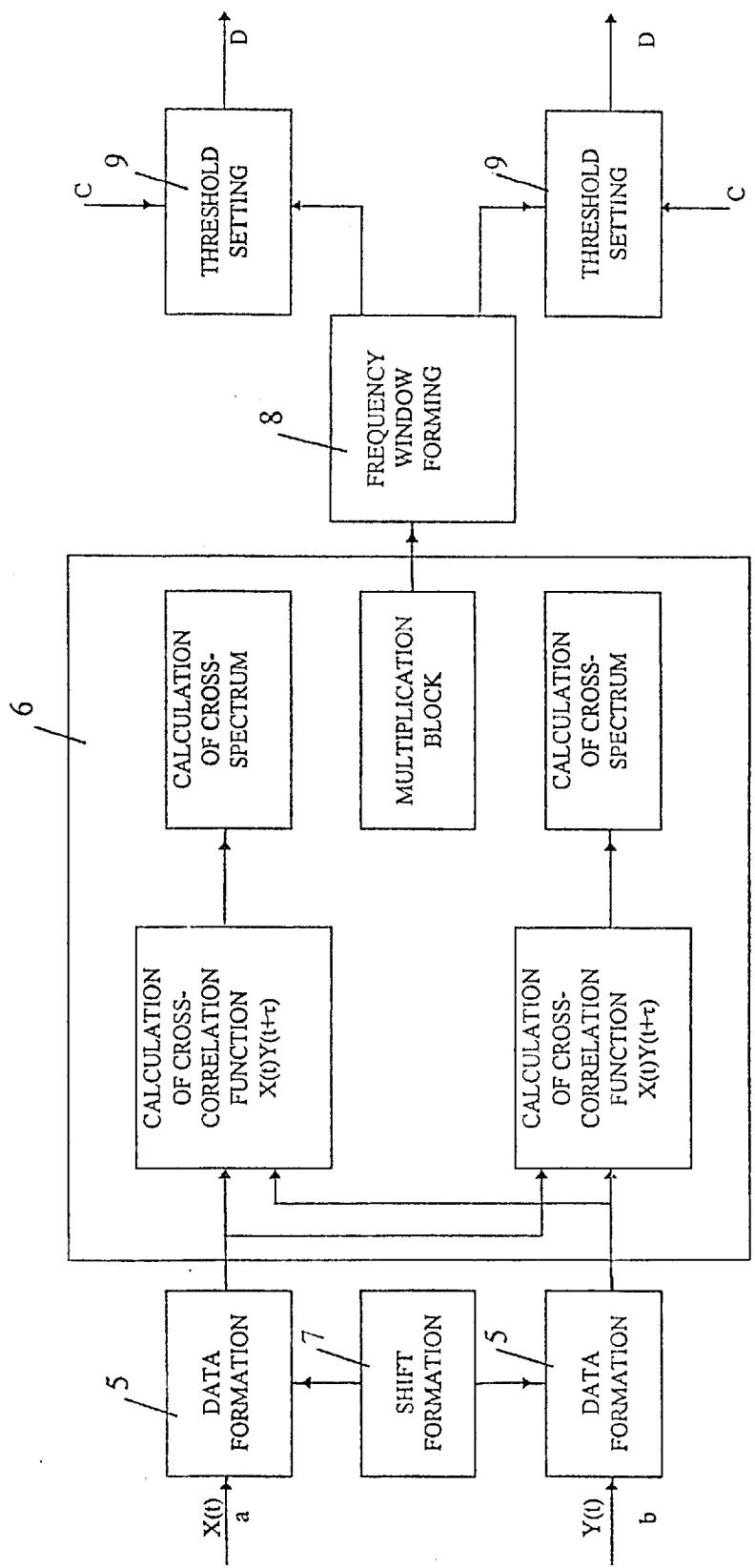
FIG. 5 is a view showing a flow chart of a joint processing of rhythmical components separated from a pair of different signals to be analyzed.

FIG. 5 shows a flow chart of the joint (cross-correlation and cross-spectral) processing of a pair of signals generated by the analyzed physiological systems.

In order to determine the power of the spectral component of the cross-spectra in the selected frequency range, two arrays of data with a predetermined duration for example 1024 seconds are formed in block 5. The procedure of the joint cross-correlation and cross-spectral processing includes spectral analysis of rhythmical components of parameter variations, which are equal for all pairs of the analyzed signals, and is performed in the block 6. The changes of the functional state of a human organism which are caused by a certain type of its activity are characterized by the average power of the spectrum in one or several frequency windows selected from the whole frequency band in block 8. In order to determine the current changes of the functional state of organism, the cross-correlation and cross-spectral analysis is performed repeatedly with the selected time shift, for example 32 seconds, during the whole time of evaluation. The time of analysis and the time shift between the formed arrays of data is given by the block 7.

The average power of the spectral component in each of the spectral windows is compared with a given threshold in block 9. When the given threshold is reached the signal C is generated.

The utilization of the method of the present invention for practical applications can be illustrated by following examples:

1. Evaluation of influence of physical load during exercising on the bicycle exerciser on the functional state of the person Under the evaluation of the changes on the functional state of the person, a preliminary processing of the signals EKG and respiration was performed in accordance with the flow chart of FIG. 4. Subsequent processing was performed in accordance with the flow chart of FIG. 5.

In order to determine changes in the functional state of the person, the signals were analyzed before the beginning of exercising when the person was in a relaxed state characterized as a background mode, and also during its work on the bicycle exerciser. The epoch analysis of the rhythmical components of the parameter variations were selected equal to 1024 seconds so that their spectral analysis was performed within the range with the periods from 8 minutes 32 seconds to 16 seconds. For performing the spectral analysis, formulas of fast Fourier transform for 128 values (FFT 128) were utilized. In this case the interval of the discreting was 8 seconds, and correspondingly the time of the averaging in the block 3 of FIG. 4 was also 8 seconds. The successive time shift between the analyzed arrays of data was selected equal to 32 seconds. The duration of observation of the person in each period of the test was 35 minutes. These parameters were formed by the block 7 in FIG. 5.

Figure 6:
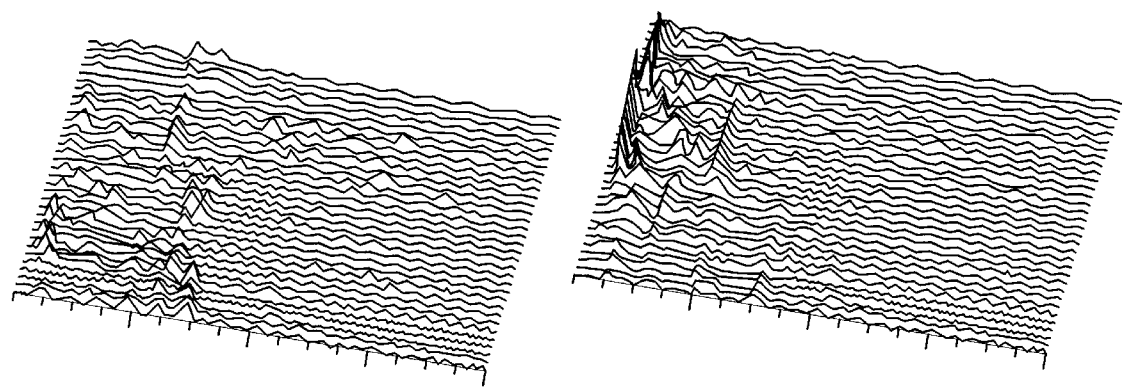
FIG. 6 is a view showing cross-spectra in a whole analyzed frequency band which characterize the process of interaction of a cardiovascular system and a respiration system in a background mode (left diagram) and during the process of physical loading on an exercising bicycle in 25 minutes (right diagram)
Figure 7:
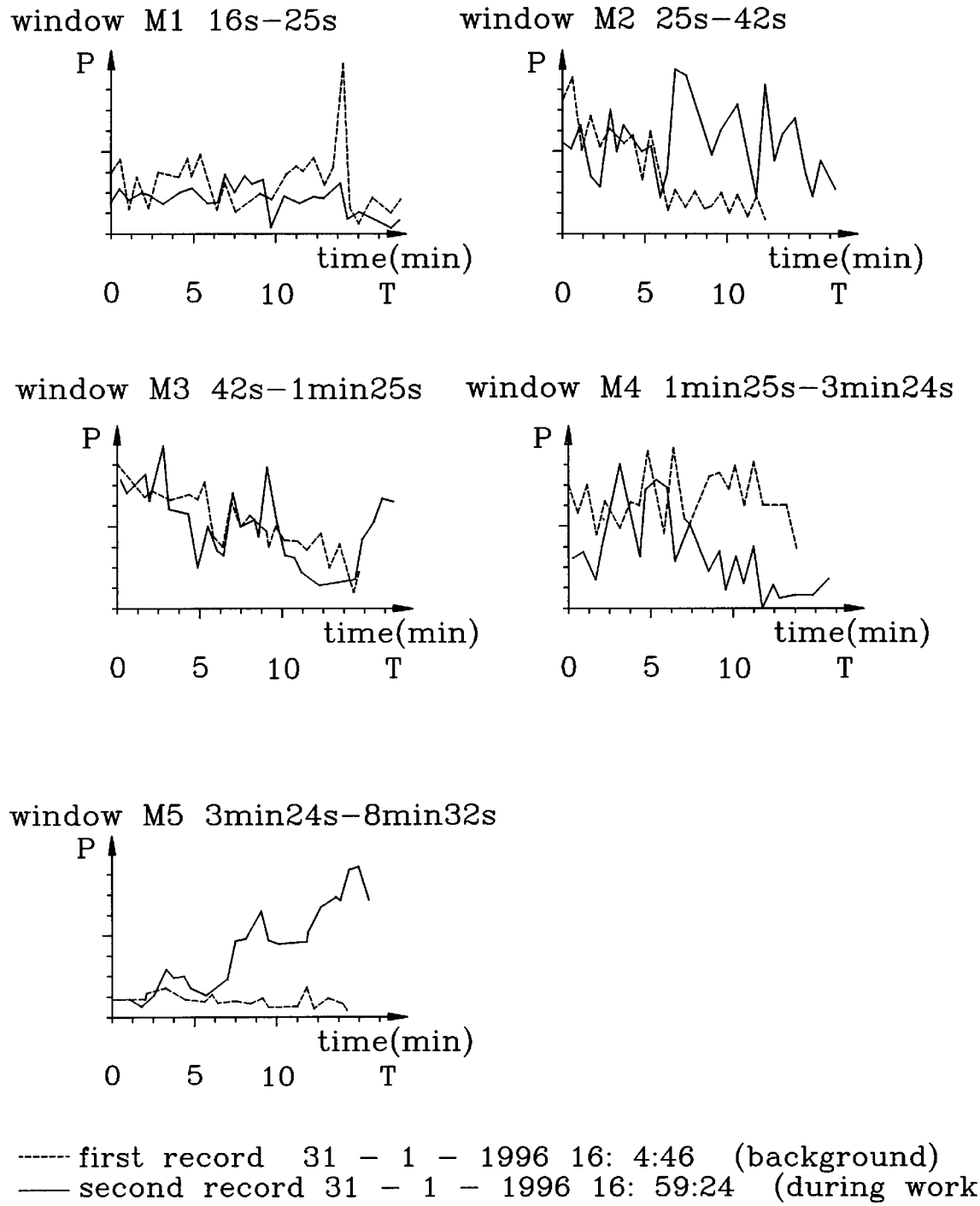
FIG. 7 is a view showing the characteristics of cross-spectra of rhythmical components in five frequency windows in a background mode (solid lines) and during the process of loading on the exercising bicycle in 25 minutes (broken lines)

The cross-spectra power at the output of the block 8 in FIG. 5 characterized the rhythmical components in the whole frequency band are given in FIG. 6. The left diagram shows the background state of the person, while the right diagram shows the state of the person during working on the bicycle exerciser. The lower spectrograms were obtained as a result of the processing of the first array of data with duration of 1024 seconds. The subsequent spectrograms correspond to the time shift by 32 seconds.

The numbers N of the partial filters FFT are plotted in the spectrogram along the axis X starting from the second (N=2, 3 . . . 63), while the time T is plotted along the axis Y, and the spectral component power is plotted along the axis Z. In the block 8 of FIG. 5, the whole frequency band is subdivided into five frequency windows, in which the current value of the average power was measured: M1 (wave period 16–25 seconds), M2 (25–42 seconds), M3 (42 seconds–1 minute 25 seconds), M4 (1 minute 25 seconds–3 minutes 24 seconds), and M5 (3 minutes 24 seconds–8 minutes 32 seconds).

In order to clearly see a comparison of the processes interaction in two modes of test, the current values of the average spectral power for the background mode are shown by a solid curve and for the mode of work on the bicycle exerciser are shown by a broken curve. As can be seen from the drawings, the most significant changes of the processes of interaction of the cardiovascular and the respiratory systems during the work on the bicycle exerciser when compared with the background occurs in the window M5. Therefore, in such tests it was possible to perform the analysis of the data only in this particular window.

2. Evaluation of current working capability during the process of solving complicated intellectual problems The proper duration of the work of the operator with deprivation of sleep was 56 hours and included uninterrupted cycles of 4 hours separated by an hour interval. During the interval, medical checkup was performed as well as the test of the working capability by an independent control method based on the use of the psychophysiological test. Therefore, the data obtained by the inventive method could be verified.

During this test, the processes of interactions of the central nervous system (EEG signals) and the cardiovascular system (EKG signal) were analyzed. The preliminary processing of the signals was performed in accordance with the flow chart of FIG. 2. The epoch of analysis determined by the duration of the formed array of data was selected to be equal 1024 in block 5 of FIG. 5. The time shift between the arrays of data was 512 seconds. These parameters were given by the block 7 in FIG. 5. In order to evaluate the changes of the functional state of the operator or his working capability an average power of the spectra was measured within the wave range 1 minute 25 seconds–3 minutes 24 seconds (window M4) in the block 8 of FIG. 5.

Figure 8:
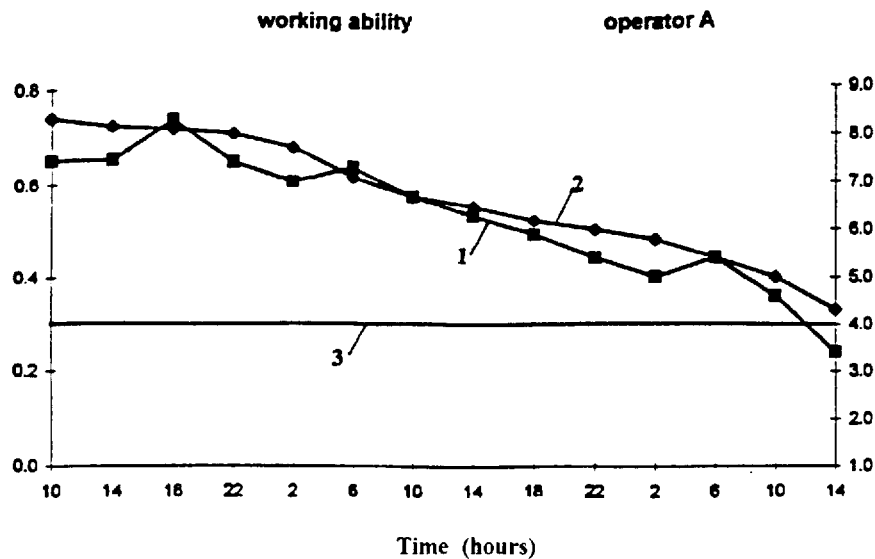
FIG. 8 is a view showing characteristics of working capability of two operators during the process of solving complicated intellectual problems in 56 hours without sleep, obtained by analysis of interaction processes of cardiovascular and respiratory systems (curves 1), with showing of results of psychophysiological tests for verification purposes (curves 2).
Figure 8:
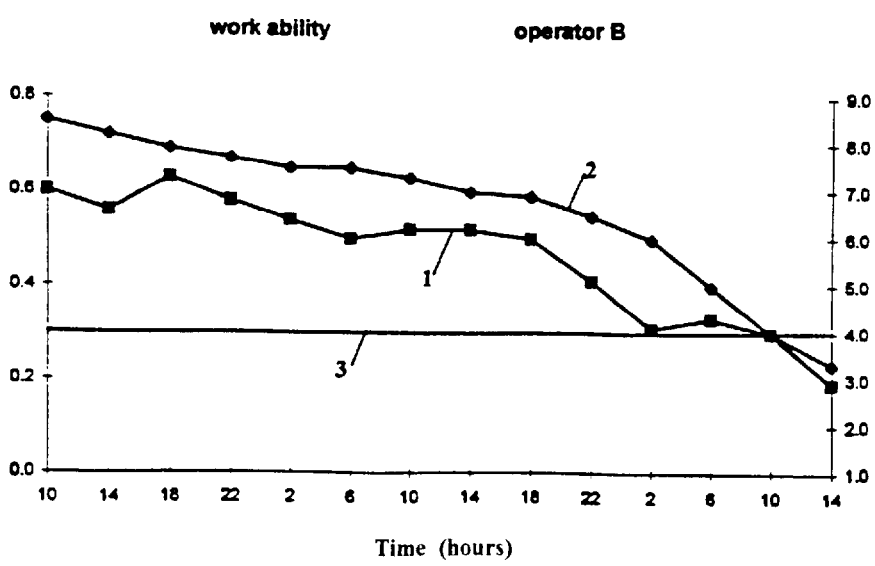

FIG. 8 shows the diagrams of the current working capability for two operators obtained with the method in accordance with the present invention and by means of the control method. The curve 1 represents the average spectral power at the output of the block 8; the curve 2 represents evaluations with psychophysiological test.

Under the tests a threshold equal to the reduction of the working capability 2.5 times was set. When the threshold has been reached, in the block 9 a corresponding signal was generated.

It will be understood that each of the elements described above, or two or more together, may also find a useful application in other types of methods and constructions differing from the types described above.

While the invention has been illustrated and described as embodied in a method of and apparatus for quantitative evaluation of current changes in functional status of human organism, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of quantitative evaluation of current changes in a functional state of a human organism, comprising the steps of evaluating characteristics of interaction processes of at least two different physiological systems of the organism, said evaluating including joint evaluating of characteristics of interaction processes of at least two different physiological systems of the organism by means of joint analyzing of parameters of at least one of electrophysiological signals, physiological processes, and electrophysiological signals and physiological processes characterized two different physiological systems, said joint evaluating including demodulating of said at least one of electrophysiological signals, physiological processes, and electrophysiological signals and physiological processes of said two different physiological systems for isolating variations of parameters of said at least one of electrophysiological signals and physiological processes of said at least two different physiological systems, measuring of current values of said variations of said parameters, and jointly cross-correlating and cross-spectral processing of the measured current values of said variations of said parameters of said at least one of electrophysiological signals, physiological processes, and electrophysiological signals and physiological processes of said at least two different physiological systems.

2. A method as defined in claim 1; and further comprising the step of averaging the current values of the variations of the parameters within chosen equidistant time intervals when the at least one of electrophysiological signals and physiological processes are uninterrupted.

3. A method as defined in claim 1; and further comprising the step of interpolating the current values of the variations of the parameters within chosen equidistant time intervals, when the at least one of electrophysiological signals and physiological processes are discrete but not equidistant.

4. A method as defined in claim 3; and further comprising the step of consequently averaging data within equidistant time intervals that are multiples of the previously chosen intervals of at least one of averaging and interpolating.

5. A method as defined in claim 4; and further comprising the step of forming at least two data arrays with equal time intervals and an equal duration corresponding to at least one of the analyzed electrophysiological signals and physiological processes.

6. A method as defined in claim 1, wherein said step of cross-correlating and cross-spectral processing includes estimating of an average power of a cross-spectrum in at least one frequency window isolated from a whole frequency band of the cross-spectrum in connection with a given task of evaluation of the current changes in the state of the human organism.

7. A method as defined in claim 6, wherein said step of estimating of the average power includes averaging only those spectral power components in a frequency window that exceeds a given threshold level chosen independently for each frequency window.

8. A method as defined in claim 1; and further including the step of choosing a value of a time shift of a further analysis epoch in relation to a beginning of a previous analysis epoch; and repeating all cycles many times within a given time interval in which the evaluating of the changes in a state of the organism is done.

9. A method as defined in claim 8; and further comprising the step of making a decision about achieving a given evaluation of the changes in a state of the organism by comparing current values of an average power of a cross-spectrum in at least one chosen frequency window with a threshold level conditioned by a given task.

10. An apparatus for quantitative evaluation of current changes in a functional state of a human organism, comprising means for evaluation of characteristics of interaction processes of at least two different physiological systems of the organism, said means for evaluation including means for demodulating at least one of electrophysiological signals, physiological processes, and electrophysiological signals and physiological processes as for isolating variations of parameters of said at least one of electrophysiological signals physiological process, and electrophysiological signals and physiological processes of said at least two different physiological systems, means for measuring current values of the variations of the parameters of the at least one of electrophysiological signals, physiological processes, and electrophysiological signals and physiological processes of the at least two different physiological systems, and means for joint-correlation and cross-spectral processing of the measured current values of the variations of the parameters of the at least one of electrophysiological signals, physiological processes, and electrophysiological signals and physiological processes of the at least two different physiological systems.

11. An apparatus as defined in claim 10, comprising means for averaging the current values of the variations of the parameters within chosen equidistant time intervals, when the least one of electrophysiological signals and physiological processes are uninterrupted.

12. An apparatus as defined in claim 10, further comprising means for interpolating the current values of the variations of the parameters within chosen equidistant time intervals, when the at least one of electrophysiological signals and physiological processes are discrete by not equidistant.

13. An apparatus as defined in claim 12, and further comprising means for consequently averaging data within equidistant time intervals that are multiples of the previously chosen intervals of at least one of averaging and interpolating.

14. An apparatus as defined in claim 13, and further comprising means for forming at least two data arrays with equal time intervals and an equal duration corresponding to the at least one of the analyzed electrophysiological signals and physiological processes.

15. An apparatus as defined in claim 14, wherein said means for cross-correlation and cross-spectral processing is formed so as to estimate an average power of a cross-spectrum in at least one frequency window isolated from a whole frequency band of the cross-spectrum in connection with a given task of evaluation of the current changes in the state of the human organism.

16. An apparatus as defined in claim 15, wherein said means for estimating the average power is formed so as to provide averaging only those spectral power components in the frequency window that exceeds a given threshold level chosen independently for each frequency window.

17. An apparatus as defined in claim 10; and further comprising means for choosing a value of a time shift of a further analysis epoch in relation to a beginning of a previous analysis epoch, and repeating all cycles many times within a given time interval in which the evaluating of the changes in a state of the organism is done.

18. An apparatus as defined in claim 17; and further comprising means making a decision about achieving a given evaluation of the changes in the state of the organism by comparing current values of an average power of a cross-spectrum in each at least one chosen frequency window with a threshold level conditioned by a given task.

* * * * *